United States Patent
Muccini et al.

(10) Patent No.: US 7,250,513 B2
(45) Date of Patent: Jul. 31, 2007

(54) BLUE EMITTING TRIS (8-OXOQUINOLINE) ALUMINUM (III) (ALQ$_3$)

(75) Inventors: Michele Muccini, Bologna (IT); Maria Antonietta Loi, Quartu Sant'elena (IT); Norberto Masciocchi, Como (IT); Angelo Sironi, Milan (IT)

(73) Assignees: Consiglio Nazionale Delle Ricerche, Rome (IT); Universita' Degli Studi Di Milano, Milan (IT); Universita' Degli Studi Dell'Insubria, Varese (IT)

( * ) Notice: Subject to any disclaimer, the term of this patent is extended or adjusted under 35 U.S.C. 154(b) by 28 days.

(21) Appl. No.: 10/517,203

(22) PCT Filed: Jun. 12, 2003

(86) PCT No.: PCT/EP03/06197

§ 371 (c)(1),
(2), (4) Date: Dec. 8, 2004

(87) PCT Pub. No.: WO03/106422

PCT Pub. Date: Dec. 24, 2003

(65) Prior Publication Data

US 2005/0248263 A1    Nov. 10, 2005

(30) Foreign Application Priority Data

Jun. 14, 2002  (IT)  .................. MI2002A1330

(51) Int. Cl.
C07D 403/14   (2006.01)
C07D 401/14   (2006.01)

(52) U.S. Cl. .............................. 546/7; 546/8

(58) Field of Classification Search .................... 546/7, 546/8; 428/917, 1
See application file for complete search history.

(56) References Cited

OTHER PUBLICATIONS

Chemical Abstracts, vol. 117, No. 16, Oct. 19, 1992 Columbus, Ohio, US; abstract No. 160319, Mori, Yasushi et al: "Organic electroluminescent diode element" XP002254143 abstract & JP 04 085388 A (Toshiba K.K., Japan) Mar. 18, 1992.

Kushto, G.P. et al: "Characterization of the chemistry that occurs at the Alq3/alkali metal halide heterointerface using quantum chemical analyses" Proceedings of SPIE-The International Society for Optical Engineering (Jul. 30, -Aug. 01, 2001), vol. 4464(Organic Light-Emitting Materials and Devices V), 374-382, 2002 XP008021266 the whole document.

Brinkmann M. et al.: "Correlation between molevular packing and optical properties in different crystalline polymorphs and amorphous thin films of mer-tris (8-hydroxyquinoline) aluminum(III)" Journal of the American Chemical Society., vol. 122, No. 21- May 31, 2000 pp. 5147-5157, XP002254141 American Chemical Society, Washington DC., US ISSN: 0002-7863 cited in the application the whole document.

Braun M. et al.: "A new crystalline phase of the electroluminescent material tris(8-hydroxyquinoline) aluminum exhibiting blueshifted fluorescence" Journal of Chemical Physics, vol. 114, No. 21, 2001, pp. 9625-9632, XP008021268 New York, NY, US ISSN: 0021-9606 cited in the application the whole document.

Cölle M. et al.: "The structure of the blue luminescent delta-phase of tris (8-hydroxyquinoline)aluminium(III)" Chemical Communications., No. 23, —Dec. 7, 2002 pp. 2908-2909, XP002254142 Royal Society of Chemistry., GB ISSN: 1359-7345 the whole document.

Cölle M. et al: "Preparation and Characterization of Blue-Luminescent Tris(8-Hydroxyquinoline)Aluminum (ALQ3)" Advanced Functional Materials, Wiley Intersciences, Wienheim, DE, vol. 13, No. 2, Feb. 2003, pp. 108-112, XP001143601 ISSN: 1616-301X the whole document.

*Primary Examiner*—Charanjit S. Aulakh
(74) *Attorney, Agent, or Firm*—Modiano & Associati; Albert Josif; Daniel O'Byrne

(57) ABSTRACT

Process for the preparation of the facial isomer of tris(8-oxoquinoline) aluminum(III) (Alq$_3$), comprising the step of heating α-Alq$_3$ in solid phase at a temperature equal to or higher than 350° C. but lower than 420° C., to obtain a mixture of γ-Alq$_3$ and δ-Alq$_3$.

5 Claims, 4 Drawing Sheets
(3 of 4 Drawing Sheet(s) Filed in Color)

BLUE EMITTING TRIS (8-OXOQUINOLINE) ALUMINUM (III) (ALQ$_3$)

BACKGROUND OF THE INVENTION

The present invention relates to the isolation of the facial stereoisomer of the electroluminescent molecule tris(8-oxoquinoline)aluminum(III) (Alq$_3$), its mass production and its characterization in solution and in the solid state.

The first highly efficient and low-voltage-driven organic electroluminescent devices (OLED), have been reported by Tang and Van Slyke (1), and were based on Alq$_3$. Fifteen years later, Alq$_3$ is still a key electroluminescent compound, widely used in commercial devices and has become the prototype of a whole class of materials used as active layers in electroluminescent devices. Recently, significant improvements in device efficiency and stability have been obtained (2–6), and many efforts have been spent in order to extend and modify the typical green emission of Alq$_3$-based OLEDs, using multilayers structures and chemical doping (7–9).

Tris-chelated octahedral complexes (such as Alq$_3$) can exist in the fac or mer isomeric forms. In the case of trisoxoquinoline complexes (Mq$_3$), only mer stereoisomers have been reported and characterized. The only reported example of a non-mer isomer is the Sbq$_3$ complex (10) which, however, is not octahedral, thanks to the presence of a stereochemically active lone pair.

In the Alq$_3$ molecule, the possible existence of different geometrical isomers is still an unresolved issue. Despite of the many investigation efforts during several years (11–14), the facial stereoisomer of Alq$_3$ has never been directly observed. Invariably, spectroscopic studies on matrix-isolated molecules, solutions and polymorphic crystal phases (13, 15) have evidenced the existence of the green-emitting mer isomer only. Curioni et al. have theoretically predicted through computational models (16) that the fac isomer is less stable ($\Delta E \approx 4$ kcal/mol) than the mer isomer and that it possesses a 0.3 eV higher energy gap (HOMO-LUMO), with a dipolar moment of 7 Debye (16).

Mer-Alq$_3$ crystallizes as $\alpha$ e $\beta$ phases (and in a number of clathrates), whose optical properties are determined by the nature of the $\pi$-$\pi$ intramolecular contacts (15). In addition, partial crystallographic information on two phases, generated at elevated temperatures, called $\gamma$ e $\delta$, has been reported (15, 17).

SUMMARY OF THE INVENTION

The main task of the present invention in the isolation of the facial isomer of Alq$_3$ (later shown to be a blue-emitting species) both in solution and in the solid state.

The aim of the present invention is to provide a procedure which allows to prepare large quantities of the blue-luminescent $\gamma$ e $\delta$ phases, both containing the elusive facial isomer of Alq$_3$.

Another aim of the present invention in to provide a method capable to stabilize the facial isomer of Alq$_3$ in solution.

One further aim of the present invention is to provide a method for obtaining blue-emitting thin films of Alq$_3$.

Another aim of the present invention is to provide blue-emitting electroluminescent devices based on Alq$_3$.

The above-mentioned aims and other aims which will become evident from the following descriptions have been reached through the solid-state synthesis of the facial isomer ($\gamma$-Alq$_3$) upon heating $\alpha$-Alq$_3$ at temperatures higher than 350° C., but lower than 420° C. (typically 390° C.), followed by its transformation into the $\delta$-Alq$_3$ phase by suspending the product obtained by heating in organic solvents (for example, acetone) and maintaining the suspension at room temperature.

Typically, heating of solid phase $\alpha$-Alq$_3$ is performed with a temperature gradient of 10° C./min in the 50 to 350° C. temperature range.

Preferably, subsequent heating in the 350° C. to 390–420° C. range is performed with a temperature gradient of 1° C./min.

As a further aspect, the present invention offers a procedure for the preparation of thin films of $\delta$ e $\gamma$-Alq$_3$, which comprises the preliminary preparation of $\delta$ e $\gamma$-Alq$_3$ solutions (for example, in CHCl$_3$) at temperatures lower than $-10°$ C., followed by the deposition of a thin layer of such solution on a substrate and followed by the fast solvent evaporation.

Solvent evaporation can also be accomplished at room temperature.

In the following, we report the direct observation of the fac isomer of the Alq$_3$ molecule by NMR spectroscopy as well as the key steps for its isolation and massive production, through a solid-solid reaction starting from the commercial ($\alpha$-Alq$_3$) material. The optical emission properties of the fac isomer in solution, both in polycrystalline powders and films, are compared with those of the mer isomer. The crystal structure of the fac isomer in the $\gamma$ and $\delta$ phases has been determined by X-ray powder diffraction methods (XRPD), which evidences the absence of $\pi$-$\pi$ intermolecular contacts between oxyquinoline ligands.

The facial (fac) isomer shows a blue emission rather different from the green light emission typical for the meridianal (mer) isomer.

A phase transformation diagram and a production method for the fac isomer is provided, starting from powders of the mer isomer.

The fac isomer crystallizes in two polymorphic species, the structures of which have been resolved by ab-initio X-ray powder diffraction methods. Both crystal phases show blue emission $\gamma$ and $\delta$-Alq$_3$ are the only known examples of Mq$_3$ species containing, in the solid state, the fac isomer.

The solution of the longstanding issue of the Alq$_3$ isomery opens the way to the development of blue-emitting electroluminescent devices based on Alq$_3$.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is described with more detail with the aid of the following figures:

FIG. 4: crystal packing of the triclinic crystals of $\delta$-Alq$_3$, viewed down [001]. At this drawing resolution, the crystal structure of the trigonal $\gamma$-Alq$_3$ phase is rather similar.

Figure 1:
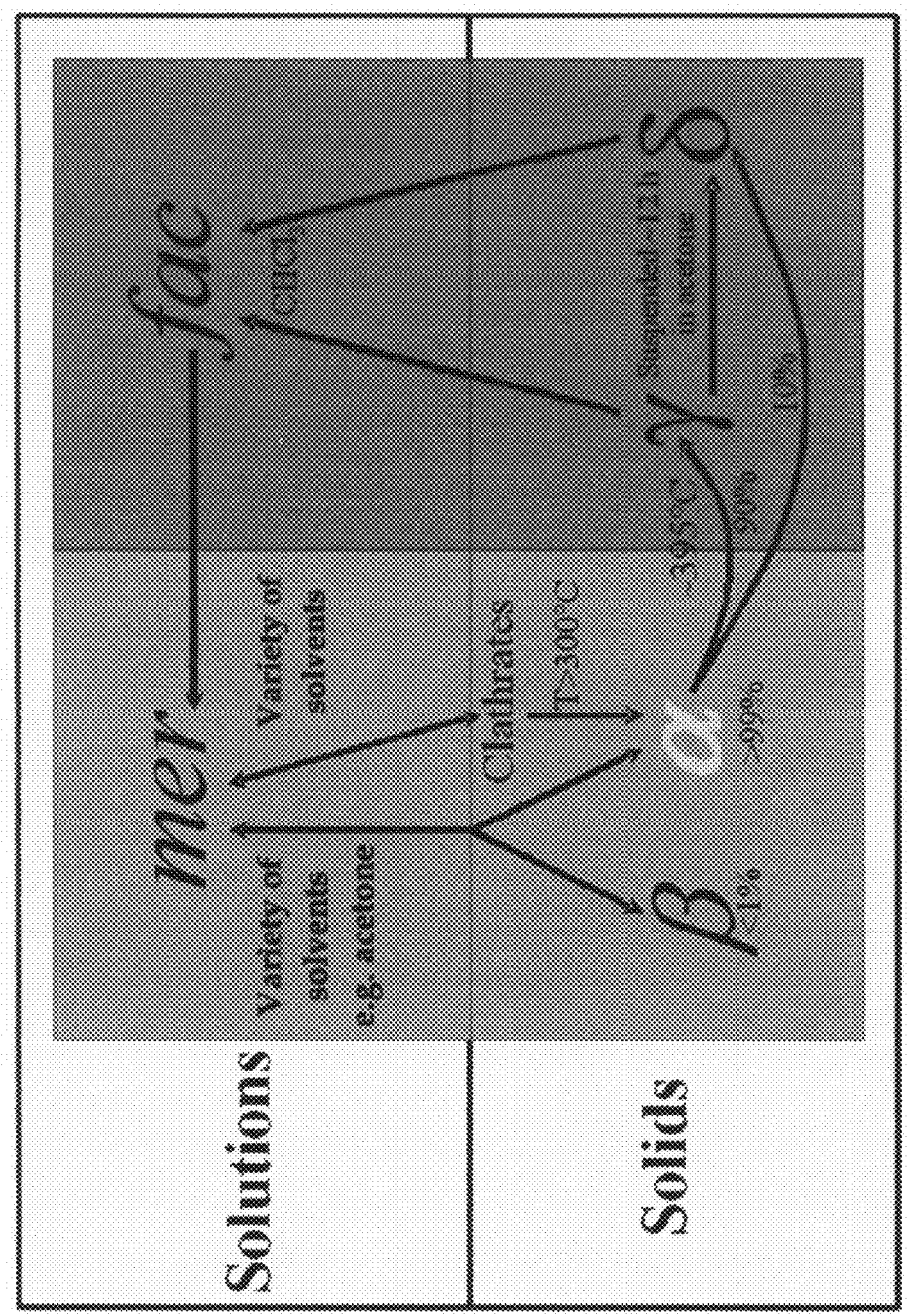
FIG. 1: phase transformation diagram for Alq$_3$.

DESCRIPTION OF THE PREFERRED EMBODIMENTS $Alq_3$ Isomery. Polycrystalline powders of α-$Alq_3$ are transformed predominantly into the γ phase upon heating at a temperature between 390° C. and 420° C. at atmospheric pressure. We discovered that a few drops of liquid acetone favor the transformation of the γ phase into the δ phase, while seeding of supersaturated solutions of mer-$Alq_3$ with nuclei of γ (or δ) do not afford the δ phase. These experimental evidences have suggested the existence of a different $Alq_3$ isomer and prompted for new systematic spectroscopic and structural analyses. The results of these investigations are reported in the phase transformation diagram depicted in FIG. 1, which shows the existence of four distinct solid phases for (unsolvated) $Alq_3$, based on the existence of two different stereoisomers. The fac isomer can only be obtained by a solid state reaction (blue arrow). However, diluted solutions of the fac isomer can be obtained from the γ (or δ) phases at low temperatures, given that it is kinetically stable below −10° C.

At room temperature, independently from the starting material (α phase, γ phase or δ phase), solution $^1$H and $^{13}$C-NMR experiments have shown that mer-$Alq_3$ is the only present species. However, upon suspending solid γ- or δ-$Alq_3$ powders in $CDCl_3$ at a temperatures of −50° C., $^1$H-NMR signals show the existence of only the fac-$Alq_3$ isomer. This neatly shows that γ- and δ-$Alq_3$ contain the fac isomer, which is kinetically stable, in the solid state, at room temperature.

Figure 2:
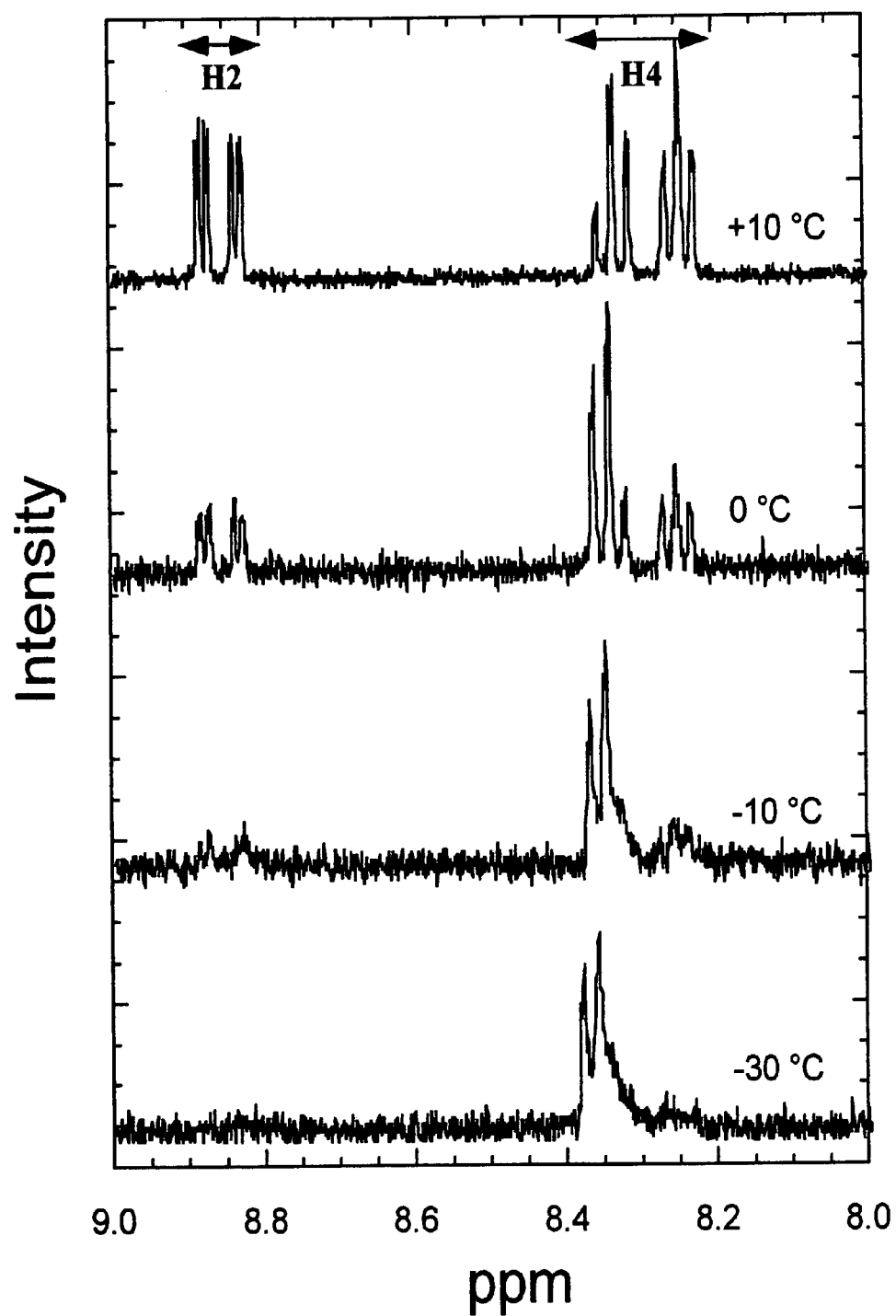
FIG. 2: $^1$H NMR spectra (8–9 ppm range, at different temperatures) of $\delta$-Alq$_3$ dissolved in CDCl$_3$.

From the spectra shown in FIG. 2 one can observe, at low temperatures, the absence of the H2 signals near δ 8.8 ppm, which, coupled with the fact that only the (magnetically equivalent) H4 nuclei are observed, shows that only the fac isomer is present. The increase of the signal-to-noise ratio observed upon heating the solution is a manifestation of the progressive transformation of the fac isomer into the more soluble mer-$Alq_3$.

Moreover, the spectra reported in FIG. 2 show that such isomerization begins at temperatures above ca. −10° C. It is worth noting that solutions prepared at room temperature from δ-$Alq_3$ only contain the mer isomer as a result of the rapid fac to mer transformation.

Figure 3:
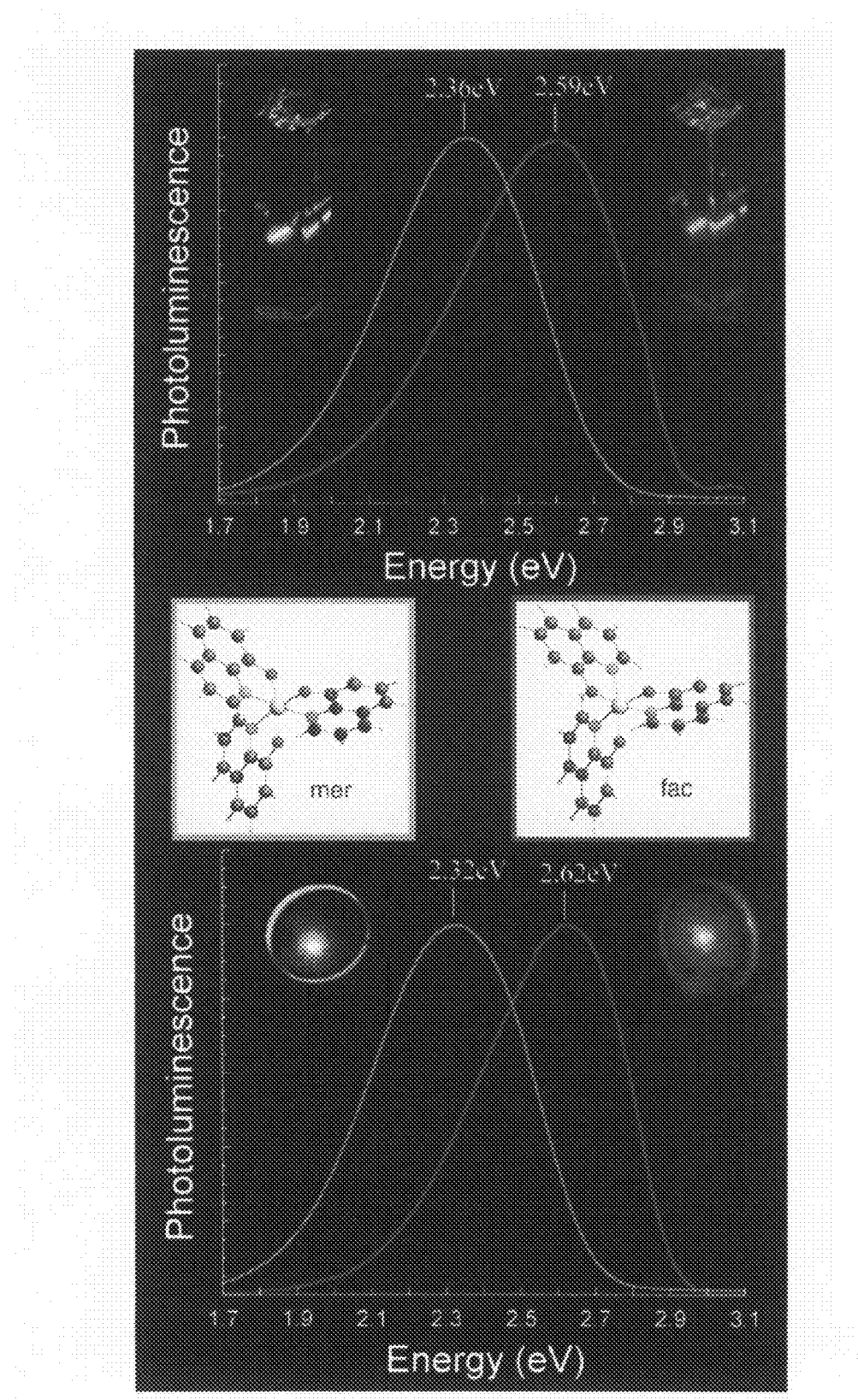
FIG. 3: top: photoluminescence spectra of fac and mer Alq$_3$ solutions, excited by an ultraviolet laser beam; bottom: photoluminescence spectra of $\alpha$- e $\gamma$-Alq$_3$ in the form of films, obtained from solutions and illuminated by a UV laser beam. The inserts show the molecular structures of the fac and mer isomers.

The photoluminescence spectra of solutions of mer- and fac-$Alq_3$ are shown in FIG. 3—top. The fac-$Alq_3$ solution has been prepared by dissolving powders of the γ or δ phases in $CHCl_3$ at −50° C. The photoluminescence of fac-$Alq_3$ in solution at −50° C. is centered at 2.59 eV and has a brilliant blue color. The spectral position of the photoluminescence does not change at temperatures below −10° C., while at higher temperatures it progressively shifts towards lower energies. It has been observed that the spectral emission maximum constantly decreases with increasing temperature, reaching a minimum value of 2.36 eV (green) at room temperature. This is in agreement with the NMR spectroscopic results, which show conversion of fac into mer at temperatures above −10° C. From the photoluminescence spectra, we found that the transformation is complete after a few hours at room temperature.

Thus, the photoluminescence spectral emission features provides a characteristic fingerprint of each isomer.

Solid-solid Transformations. On the basis of ab-initio quantomechanical computations, in the gas phase, the mer isomer is ca. 4 kcal/mol more stable than the fac isomer, but has significantly lower dipolar moment (4.1 vs. 7.1 Debye). If we assume that this also holds in solution, we can easily explain why the solution chemistry of $Alq_3$ is dominated by the mer isomer: in other words, one cannot obtain solutions of fac-$Alq_3$ through a chemical process in solution. These results are fully in agreement with the long known $^1$H-NMR experiments, which revealed the mer isomer only at all investigated temperatures. (11). Upon increasing the temperature in the solid state, small energy differences can be overcome by entropic contributions, eventually assisted by cavity effects or a more efficient crystal packing. Indeed, the solid state transformation of mer into fac, starting from the α phase, occurs only near 390° C. Surprisingly, the γ phase, which is indefinitely stable in the solid state, can be easily transformed into the δ phase, at room temperature, if a few drops of liquid acetone are added. The acetone molecules give a limited mobility to the fac molecules which, well before isomerization, crystallize as the denser and more stable δ phase.

Crystal data for γ-$Alq_3$: $C_{27}H_{18}AlN_3O_3$, molar weight 409.43 g/mol, trigonal, space group P-3, a=14.3807(6), c=6.2107(4)Å; V=1112.3(1)Å$^3$, Z=2; $\rho_c$=1.371 g/cm$^3$; $R_{wp}$ and $R_p$: 0.133 and 0.102 for 3501 data collected in the 5<2θ<75° range. $R_{Bragg}$ 0.037.

Crystal data for δ-$Alq_3$: $C_{27}H_{18}AlN_3O_3$, molar weight 409.43 g/mol, triclinic, space group P-1, a=14.44479(9), b=13.2620(7); c=6.1887(4) Å; α=95.865(5); β=88.613(5); γ=113.922(4)°; V=1078.1(1)Å$^3$, Z=g/cm$^3$; $R_{wp}$ and $R_p$: 0.161 and 0.124 for 3501 data collected in the 5<2θ<75° range. $R_{Bragg}$ 0.061.

Figure 4:
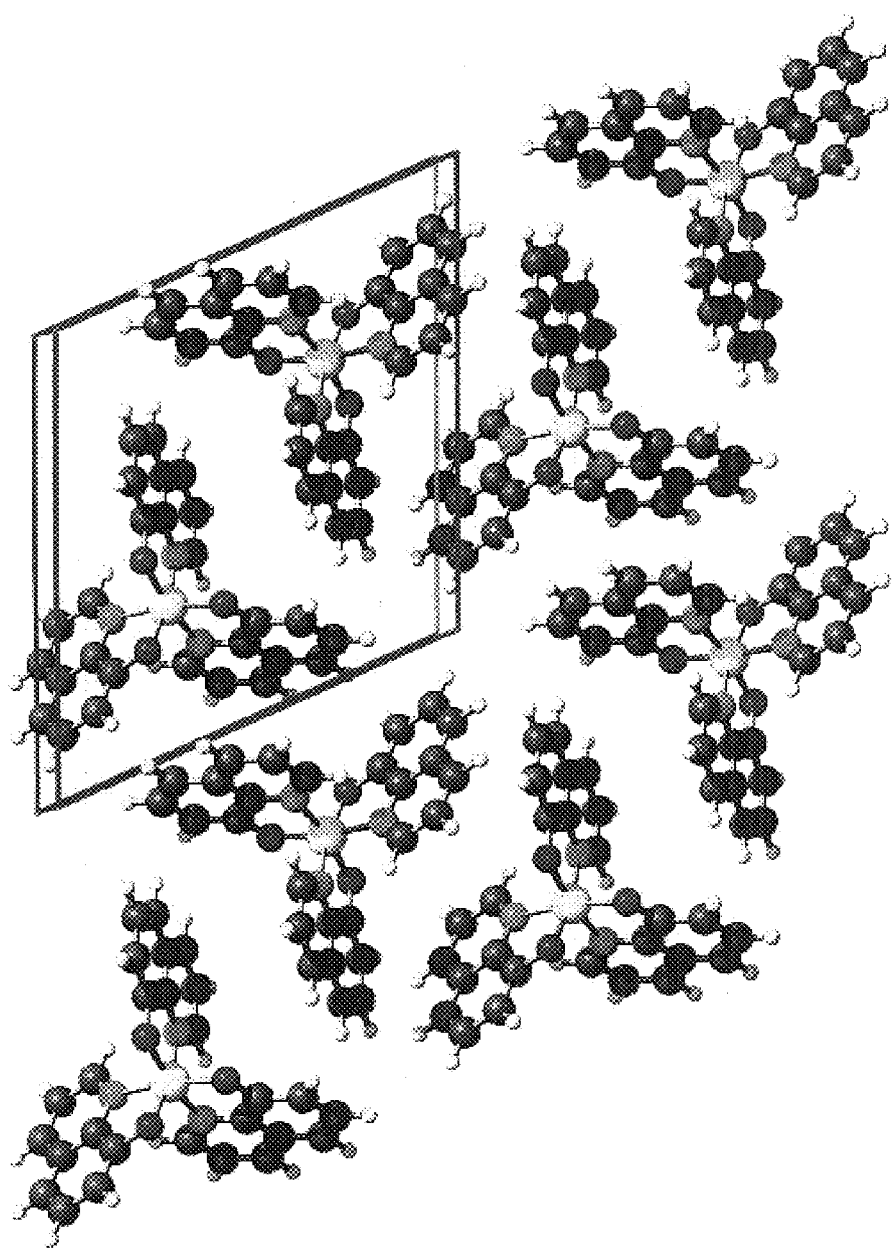

Crystals of γ-$Alq_3$ belong to the trigonal space group P-3. Fac-$Alq_3$ shows $C_3$ symmetry. δ-$Alq_3$ is triclinic, space group P-1, thus its three oxoquinoline ligands are crystallographically independent. FIG. 4 shows the pseudo-trigonal crystal packing of δ-$Alq_3$. The crystal structure of γ-$Alq_3$ is similar, with the molecules lying on threefold crystallographic axes of the trigonal space group P-3. The two phases are correlated by a proper group-subgroup relationship, since the δ phase can simply be obtained by removing the threefold axes of the γ phase, but maintaining all inversion centers. The small differences in the crystal packings of γ- and δ-$Alq_3$ are evident in their Raman spectra, which contain the same intramolecular phonon modes, but different lattice modes (20). The optical emission spectra of γ- and δ-$Alq_3$ are identical, as later discussed.

α-$Alq_3$ (15), γ- and δ-$Alq_3$ possess similar lattice parameters, thus showing that different stereoisomers can adopt similar packing modes. The common motif is the presence of chiral columns of $[Alq_3]_\infty$, parallel to the c axis, pseudotrigonally packed in the ab plane. In all these phases, thanks to their centrosymmetric nature, molecules of $(\pm)Alq_3$ and the columns of opposite chirality coexist in an equimolar ratio.

Solid state optical properties. The possibility of preparing stable blue emitting thin films of $Alq_3$ derives from the comprehension of the $Alq_3$ isomery and from the phase transformation diagram. The availability of stable solutions of fac-$Alq_3$ allows the preparation of films which maintain the characteristic blue emission of the fac-$Alq_3$ isomer. FIG. 3—bottom—shows films obtained by deposition of a solution of fac-$Alq_3$ and of a solution of mer-$Alq_3$ on quartz substrates. At low temperatures, the fac to mer transformation is relatively slow and allows the stabilization of the fac isomer in the solid phase after solvent evaporation, even when the substrate is kept at room temperature. FIG. 3—bottom—shows the photoluminescence spectra measured on polycrystalline powders of α-$Alq_3$ (green) and δ and γ-$Alq_3$ (blue) at 4K. As mentioned above, there is no significant difference between the photoluminescence spectra of the γ and δ phases. The spectra of α- and γ-$Alq_3$ clearly show the same vibronic progression due to the bending mode at 525 cm$^{-1}$ (21) which, in both cases, is described by a Huang-Rhys factor of ca. 2.6. This indicates that in both isomers the same strong electron-phonon coupling is present in the radiative electronic transition.

The photoluminescence spectra of the thin films of the mer and fac isomer are similar to those of the powders of α and γ (or δ) but are red-shifted and, even at low temperatures, do not show the vibronic progression. This behavior is typical in thin films of Alq$_3$ and has been interpreted in the past as a consequence of the coexistence of the two isomers (2, 16). In the light of the results here reported, the amorphous nature of the thin films of Alq$_3$ is more likely attributed to the polymorphism, rather to the racemic nature, of Alq$_3$.

The discovery of blue emitting stable phases of Alq$_3$ allows the fabrication of blue emitting efficient OLEDs based on Alq$_3$. This, together with a deeper knowledge of the optical and electronic properties of Alq$_3$, may allow the use of a unique active material in color visualization devices of the RGB (red, green, blue) type.

NMR Spectroscopy: α-Alq$_3$ can easily be dissolved in a number of organic solvents; differently, δ-Alq$_3$ shows much lower solubility. In a first series of NMR experiments, powders of α-Alq$_3$ and δ-Alq$_3$ were dissolved in CDCl$_3$ at room temperature. The $^1$H and $^{13}$C NMR spectra have been collected on a 400 MHz Bruker NMR AVANCE instrument.

The room temperature $^1$H-NMR spectrum of mer-Alq$_3$ fully agrees with that reported in (18). The molecular aggregation in solution, originally observed through fluorescence spectroscopy (15) has been confirmed from the concentration dependent chemical shifts of the "external" protons, particularly of H4. A peculiarity of this spectrum is the anomalous lowering (1.5 ppm) of the chemical shift of one of the three H2 atoms. This is due to the unique intramolecular environment of this H2 atom, pointing toward an adjacent aromatic ring. This information is of high relevance in the interpretation of the $^1$H NMR spectrum of the fac-Alq$_3$ isomer at −50° C. Indeed, the stereochemistry of fac-Alq$_3$ requires that all H2 atoms feel diamagnetic ring currents.

In a second series of NMR experiments, solid δ-Alq$_3$ has been cooled to liquid nitrogen temperature in an NMR tube. CDCl$_3$ has been added and the temperature has been raised to −50° C. at controlled rate in about 30 minute time. A series of $^1$H NMR spectra has been measured at this temperature, which demonstrated the absence of molecular isomerisation even after a few hours. Further spectra were subsequently collected upon increasing the temperature by 10° intervals, up to room temperature. 10 minutes delays have been given after each spectrum, in order to thermally stabilize the system.

The fac-Alq$_3$ isomer shows a simpler $^1$H NMR spectrum, due to its C3 symmetry. It consists of two multiplets centered near δ 8.36 ppm (H4) and δ 7.52 ppm (H6) and of many severely overlapped peaks, in the 7.1 to 7.4 ppm range (H2, H3, H5 e H7). All resonances of the H2 atoms are shifted to high fields, just as the unique H2 atom of mer-Alq$_3$ (δ 7.22 ppm, see (18)).

Powder X-ray diffraction analysis: indexing of the diffraction pattern of γ-Alq$_3$ confirmed the reported trigonal metrics and gives better figures of merit [a=14.364, c=6.208 Å; M(22)=42, F(22)=56 (0.009, 43)]. On the basis of a complete Rietveld analysis, the correct trigonal space group in not P-31 c (15) but P-3 (001 reflections being obscured by accidental overlap). We note the original assignment of γ-Alq$_3$ as based on the mer isomer was tentatively presented using a low quality XRPD pattern (not allowing a complete modeling by the Rietveld technique), together with the consideration that in the sublimed powders only mer-Alq$_3$ was present. The complete Rietveld analysis here reported determines in a definitive manner the molecular (fac) and crystal line structure of γ-Alq$_3$. Indexing of the diffraction pattern of the δ polymorph leads to a triclinic cell [a=14.503, b=13.288, c=6.208 Å; α=95.9; β=89.7; γ=114.0; M(23)=21, F (23)=53 (0.009, 47)]. The structure resolution of γ- and δ-Alq$_3$ has been performed by the simulated annealing technique (Bruker AXS 2000; Topas V2.0.). The final refinement of the structural models of biphasic mixtures have been performed on two different sets of data (Γ and Δ, rich, respectively, in γ- and δ-Alq$_3$,) collected in the 5<2θ<75° range, with step size Δ2θ=0.02°, t=60 (Γ) or 100 (Δ) s step$^{-1}$. Both in the solution and in the refinement steps we used oxyquinoline fragments of ideal geometry, hinged about the Al atom through flexible restraints [on the intramolecular contacts 1.2 Al/X and 1.3 X/X (X=N,O) of a fac stereoisomer]. The XRPD traces have been collected on a conventional powder diffractometer (Philips PW1820) equipped with Soller slits, a secondary beam graphite monochromator, and Cu-Kα radiation, λ=1.5418 Å, 40 KV, 40 mA.

The following examples are given for illustration but not limitation of the present invention.

EXAMPLES

Example # 1

Preparation of γ-Alq$_3$ (polycrystalline powders): commercial α-Alq$_3$ is heated to 395° C. using a temperature gradient of 10° C./minute in the 50–350° C. range and of 1° C./minute between 350° C. and 395° C. After maintaining the system at this temperature for some minutes, is its rapidly cooled down to room temperature. The XRPD analysis show that the resulting powders, of dark yellow color, consist of a mixture of the γ-Alq$_3$ and δ-Alq$_3$ phases. On using 15 mg of α-Alq$_3$ powders, the γ-Alq$_3$/δ-Alq$_3$ ratio is close to 10/1; such ration is not significantly modified by an increase of the heating rate up to 10° C./minute or by a decrease of the cooling rate, down to 1° C./minute. Moreover, this ratio remains unchanged by heating at the maximum pre-sublimation temperature of 410° C. The use of larger amounts of the starting material (grams), however, was found to typically afford lower γ-Alq$_3$/δ-Alq$_3$ ratios.

Example # 2

Preparation of δ-Alq$_3$ (polycrystalline powders): γ-Alq$_3$, prepared as described in the Example # 1 and thus containing already small quantities of δ-Alq$_3$, is suspended in acetone for 15 hours at room temperature with occasional stirring. Through centrifugation, the resulting light yellow powder is then recovered. The XRPD analysis shows the presence of (almost pure) δ-Alq$_3$ phase, accompanied by less than 4% residual γ-Alq$_3$. Neither the solvent volume nor the γ-Alq$_3$/δ-Alq$_3$ ratio in the starting powders have any influence on the γ-Alq$_3$/δ-Alq$_3$ ratio in the final mixture. The disclosures in Italian Patent Application No. MI2002A001330 from which this application claims priority are incorporated herein by reference.

REFERENCES

1. C. W. Tang, S. A. Van Slyke, *Appl. Phys. Lett.* 51, 913 (1987).
2. P. E. Burrows et al., *J. Appl. Phys.* 79, 7991 (1996).
3. J. Shi, C. W. Tang, *Appl. Phys. Lett.* 70, 1665 (1997).
4. L. S. Hung, C. W. Tang, M. G. Mason, *Appl. Phys. Lett.* 70, 152 (1997).

5. H. Aziz, D. Popovic, N.-X. Hu, A.-M. Hor, G. Xu, *Science* 283, 1900 (1999).
6. S. Barth et al., *Phys. Rev. B* 60, 8791 (1999).
7. Z. Shen, P. E. Burrows, V. Bulovic, S. R. Forrest, M. E. Thompson, *Science* 276, 2009 (1997).
8. Y. Hamada, *IEEE Trans. Electron Devices* 44, 1208 (1997).
9. C. W. Tang, S. A. VanSlyke, C. H. Chen, *J. Appl. Phys.* 65, 3610 (1989).
10. L. Y. Pech et al., *Zh. Neorg. Khim.* 45, 940 (2000).
11. B. C. Baker, D. T. Sawyer, *Analytical Chem.* 40, 1945 (1968).
12. J. R. Majer, J. A. Reade, *Chem. Comm.*, 58 (1970).
13. G. P. Kushto, Y. Iizumi, J. Kido, Z. H. Kafafi, *J. Phys. Chem. A* 104, 3670 (2000).
14. M. D. Halls, R. Aroca, *Can. J. Chem.* 76, 1730 (1998).
15. M. Brinkmann et al., *J. Am. Chem. Soc* 122, 5147 (2000).
16. A. Curioni, M. Boero, W. Andreoni, *Chem. Phys. Lett.* 294, 263 (1998).
17. M. Braun et al., *J. Chem. Phys.* 114, 9625 (2001).
18. H. Schmidbaur, J. Lettenbauer, D. L. Wilkinson, G. Mueller, O. Kumberger, *Zeit. Naturforschung* B46, 901 (1991).
19. P. Mei, M. Murgia, C. Taliani, E. Lunedei, M. Muccini, *J. Appl. Phys.* 88, 5158 (2000).
20. M. Muccini, M. A. Loi, G. Ruani, to be published.
21. A. Degli Esposti, M. Brinkmann, G. Ruani, *J. Chem. Phys.* 116, 798 (2002).
22. S. F. Alvarado, L. Libioulle, P. F. Seidler, *Synth. Met.* 91, 69 (1997).
23. A. Curioni, W. Andreoni, *J. Am. Chem. Soc.* 121, 8216 (1999).
24. X. L. Xu et al., *J. Appl. Phys.* 89, 1082 (2001).

What is claimed is:

1. Process for the preparation of the facial isomer of tris(8-oxoquinoline)aluminum(III) ($Alq_3$), comprising the step of heating $\alpha$-$Alq_3$ in solid phase at atmospheric pressure at a temperature equal to or higher than 350° C. but lower than 420° C., to obtain a mixture of $\gamma$-$Alq_3$ and $\delta$-$Alq_3$ both containing the facial isomer of $Alq_3$.

2. The process according to claim 1, further comprising a step of suspending said mixture in an organic solvent and keeping said suspension at ambient temperature thereby $\gamma$-$Alq_3$ of said mixture is transformed into $\delta$-$Alq_3$.

3. The process according to claim 2, wherein said organic solvent is acetone.

4. A process for the preparation of $\delta$-$Alq_3$ comprising the steps of:
   heating alpha-$Alq_3$ in solid phase at atmospheric pressure at a temperature equal to or higher than 350° but lower than 420° C., thereby a mixture of $\gamma$-$Alq_3$ and $\delta$-$Alq_3$ is obtained;
   suspending the mixture in an organic solvent, and
   keeping the suspension at ambient temperature thereby the $\gamma$-$Alq_3$ is transformed into $\delta$-$Alq_3$.

5. Process according to claim 4, wherein said organic solvent is acetone.

\* \* \* \* \*